United States Patent [19]

Burkart et al.

[11] Patent Number: 4,782,079
[45] Date of Patent: Nov. 1, 1988

[54] 2-(2,2-DIHALOETHENYL)-5-ARYLTHIOPHENE PESTICIDES

[75] Inventors: Susan E. Burkart, Trenton, N.J.; Richard B. Phillips, Riverbank, Calif.; David M. Roush, Princeton, N.J.

[73] Assignee: FMC Corporation, Philadelphia, Pa.

[21] Appl. No.: 148,194

[22] Filed: Jan. 26, 1988

Related U.S. Application Data

[63] Continuation of Ser. No. 869,472, Jun. 2, 1986, abandoned.

[51] Int. Cl.[4] ............... A01N 43/02; C07D 333/00; C07D 333/24
[52] U.S. Cl. ..................... 514/438; 514/95; 549/6; 549/78; 549/79; 549/80
[58] Field of Search ............... 514/438, 95; 549/6, 549/78, 79, 80

[56] References Cited

FOREIGN PATENT DOCUMENTS 2810262  9/1978  Fed. Rep. of Germany .
117922   2/1974  Japan ................................. 514/438

OTHER PUBLICATIONS

Chem Abst, James vol. 94 (1981), 94:174862p.
E. Campaigne, *J. Am. Chem. Soc.*, 66, 684 (1944).

Primary Examiner—Alan Siegel
Attorney, Agent, or Firm—H. Robinson Ertelt; Robert L. Andersen

[57] ABSTRACT

Thiophene derivatives of the following formula are effective as acaricides:

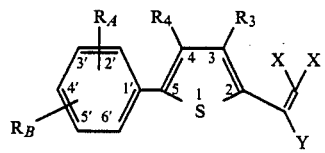

wherein $R_A$ is selected from -hydrogen, -halogen, -lower alkyl, hydroxy, -lower alkoxy, -lower alkylthio, -lower alkoxyalkoxy, -lower alkoxycarbonyl, -aryloxycarbonyl, -lower alkoxycarbonyloxy, -lower alkylsulfonyl, -lower alkylsulfonyloxy, -arylsulfonyloxy, and -lower alkyl phosphonyloxy;

$R_B$ is -hydrogen, or $R_A$ and $R_B$ together are —$C_4H_4$— bridging 2'-3' or 3'-4';

$R_3$ and $R_4$ are selected from -hydrogen, -lower alkyl, and -aryl;

X is -halogen; and

Y is selected from -hydrogen and -halogen.

14 Claims, No Drawings

2-(2,2-DIHALOETHENYL)-5-ARYLTHIOPHENE PESTICIDES

This application is a continuation of application Ser. No. 869,472 filed June 2, 1986 now abandoned.

This invention is in the field of heterocyclic organic chemical compounds which contain a thiophene nucleus. More particularly, the invention includes certain thiophene compounds per se, argicultural compositions containing the novel compounds, and the method of using a broad class of such compounds to control agricultural pests.

There is increasing scientific evidence that toxic reactions initiated by light play an important role in natural control of insect populations. In the last few years the concept of using photoactive agents as insecticides has been advanced. Such photosensitizers typically displayed insecticidal activity by catalyzing the electronic triplet to singlet conversion of molecular oxygen. The excited singlet oxygen behaves as a superoxidizing agent, destroying the insect tissues which it contacts, hence killing the insect.

According to the present invention, 2-(2,2-dihaloethenyl)-5-arylthiophene compounds of the following structural formula are photodynamic insecticides and acaricides:

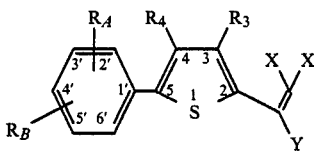

wherein $R_A$ is selected from -hydrogen, -halogen, -lower alkyl, -hydroxy, -lower alkoxy, -lower alkylthio, -lower alkoxyalkoxy, -lower alkoxycarbonyl, -aryloxycarbonyl, -lower alkoxycarbonyloxy, -lower alkylsulfonyl, -lower alkylsulfonyloxy, -arylsulfonyloxy, and -lower alkyl phosphonyloxy;

$R_B$ is -hydrogen, or $R_A$ and $R_B$ together are $-C_4H_4-$ bridging 2'-3' or 3'-4';

$R_3$ and $R_4$ are selected from -hydrogen, -lower alkyl, and -aryl;

X is -halogen; and

Y is selected from -hydrogen and -halogen.

In the aforesaid description and wherever the terms appear hereinafter, "halo" and "halogen" mean fluorine, chlorine, or bromine. The term "lower" modifying "alkyl," "alkoxy," and the like, implies a straight or branched hydrocarbon chain of 1-6, preferably 1-4, carbon atoms. The term "acyl" includes phenyl, as well as phenyl substituted with common substituents, such as alkyl and halogen.

Among the aforesaid compounds, it is preferred that $R_A$ is -hydrogen, -lower alkoxycarbonyl or -lower alkylsulfonyloxy; $R_B$ is -hydrogen; and $R_3$ and $R_4$ are independently -hydrogen or -lower alkyl. Specific preferred compounds include 2-(2,2-dibromoethenyl)-4-methyl-5-phenylthiophene, 2-(2,2-dibromoethenyl)-3,4-dimethyl-5-phenylthiophene, 2-(2,2-dichloroethenyl)-5-(naphth-1-yl)thiophene, 2-(2,2-dibromoethenyl)-5-phenylthiophene, 2-(2,2-dibromoethenyl)-5-(4-fluorophenyl)thiophene, 2-(2,2-dibromoethenyl)-5-(4-acetyloxyphenyl)thiophene, and 2-(2,2-dibromoethenyl)-5-(4-methylsulfonyloxyphenyl)thiophene.

The 2-(2,2-dihaloethenyl)-5-arylthiophene compounds of this invention are prepared by general techniques which form part of the prior art. These techniques are illustrated by the following specific examples:

EXAMPLE 6

2-(2,2-Dibromoethenyl)-4-methyl-5-phenylthiophene

Under a dry nitrogen atmosphere, N-bromosuccinimide (54.4 g, 0.31 mole) was added to a stirred solution of 3-methylthiophene (30.0 g, 0.31 mole) and carbon tetrachloride (80 mL). The reaction flask was covered with foil to exclude light. The reaction mixture was heated at reflux for four hours, then was cooled to room temperature and stirred for approximately 18 hours. The reaction mixture was filtered and the filtrate evaporated under reduced pressure leaving an oil. Purification of this oil by fractional distillation under reduced pressure yielded 38.2 g of 2-bromo-3-methylthiophene (bp 84°-85° C./36 mmHg).

A stirred mixture of 2-bromo-3-methylthiophene (15.0 g, 0.085 mole) and bis(1,3-diphenylphosphino)propane nickel(II) chloride (0.5 g, 0.009 mole) in diethyl ether (75 mL) was cooled to 0° C. Phenyl magnesium bromide (29.6 mL of a 3M solution in diethyl ether) was added slowly, causing the reaction mixture to reflux. After complete addition, reflux was continued for 15 minutes. The mixture was cooled, and approximately 100 mL of an aqueous 10% hydrochloric acid solution was added. The resultant mixture was extracted with diethyl ether, and the extract was washed with an aqueous saturated sodium bicarbonate solution. The washed extract was dried over anhydrous magnesium sulfate and filtered. The filtrate was evaporated under reduced pressure yielding 17.3 g of 3-methyl-2-phenylthiophene as a colorless oil.

To a cold (0° C.), stirred solution of 3-methyl-2-phenylthiophene (6.0 g, 0.034 mole) in dry tetrahydrofuran (80 mL) was added n-butyllithium (16.5 mL of a 2.3M solution in hexanes). After stirring at 0° C. for two hours, the mixture was cooled to −78° C. and N,N-dimethylformamide (10.5 mL, 0.14 mole) was added. The mixture was allowed to warm slowly to room temperature. Dilute hydrochloric acid was added slowly until the mixture was acidic. The acidic mixture was extracted with diethyl ether, and the extract was washed with an aqueous saturated sodium bicarbonate solution. The washed extract was dried over anhydrous magnesium sulfate and filtered. The filtrate was evaporated under reduced pressure, leaving an oil. This oil solidified upon standing in a refrigerator. Purification by recrystallization from diisopropyl ether yielded 5.0 g of 4-methyl-5-phenylthienyl-2-carboxaldehyde (mp 54°-55° C.).

A stirred mixture of 4-methyl-5-phenylthienyl-2-carboxaldehyde (2.0 g, 0.01 mole) and triphenylphosphine (5.2 g, 0.02 mole) in 50 mL of methylene chloride was cooled in an ice bath. Carbon tetrabromide (3.2 g, 0.01 mole) was added to the reaction mixture. After complete addition the ice bath was removed, and the reaction mixture was allowed to warm to room temperature and was stirred for 2.5 hours. The reaction mixture was diluted with 200 mL of petroleum ether and stirred vigorously. The mixture was filtered, and the filtrate was evaporated under reduced pressure, leaving an oil. This oil was purified by column chromatography on silica gel, eluting with petroleum ether, to yield 2.5 g of 2-(2,2-dibromoethenyl)-4-methyl-5-phenylthiophene as an oil.

Analysis:
Calc'd for $C_{13}H_{10}Br_2S$: C 43.60; H 2.81; Found: C 43.30; H 2.63.

EXAMPLE 10

2-(2,2-Dichloroethenyl)-3,5-diphenylthiophene

A stirred mixture of 2,4-diphenylthiophene (10.0 g, 0.042 mole), prepared by the method of Campaigne, *J. Am. Chem. Soc.*, 66, 684 (1944), in dry tetrahydrofuran (90 mL) was cooled to −20° C. A solution of n-butyllithium (18.8 mL of a 2.7M solution in hexanes) was added dropwise to the reaction mixture during a five minute period. After complete addition, the mixture was stirred at −30° C. for two hours, then was cooled to −78° C. N,N-Dimethylformamide (7.2 mL) was added, and the reaction mixture was allowed to slowly warm to room temperature. The reaction mixture was poured into 90 mL of an aqueous 10% hydrochloric acid solution, and the resultant mixture was extracted with methylene chloride. The extract was washed with an aqueous solution saturated with sodium chloride. The washed extract was dried over anhydrous magnesium sulfate and filtered. The filtrate was evaporated under reduced pressure, leaving a solid. Recrystallization of this solid from diethyl ether yielded 7.6 g of 3,5-diphenylthienyl-2-carboxaldehyde (mp 88°–90° C.).

To a stirred mixture of 3,5-diphenylthienyl-2-carboxaldehyde (3.0 g, 0.011 mole), triphenylphosphine (5.9 g, 0.022 mole), and zinc dust (1.5 g, 0.023 mole) in methylene chloride (90 mL) was added bromotrichloromethane (5.4 g, 0.027 mole). After addition, the mixture was stirred at room temperature for three hous. The reaction mixture was diluted with petroleum ether (300 mL), and the resultant mixture was cooled in a freezer for approximately 18 hours, causing an oily residue of the mixture was decanted from the residue. This residue was dissolved in petroleum ether (400 mL), diethyl ether (100 mL), and methyl iodide (10 mL) and stirred at room temperature for approximately 18 hours. A small amount of triphenylphosphine iodide formed and was removed by filtration. The filtrate was evaporated under reduced pressure, leaving a yellow solid. Purification of this solid by column chromatography on silica gel, eluting with n-hexane:ethyl acetate (80:20), yielded 2.3 g of 2-(2,2-dichloroethenyl)-3,5-diphenylthiophene as a solid (mp 111°–113° C.)

Analysis: Calc'd for $C_{18}H_{12}Cl_2S$: C 65.26; H 3.65; Found: C 66.68; H 4.20.

EXAMPLE 27

2-(2,2-Dibromoethenyl)-5-(4-hydroxyphenyl)thiophene

A mixture of 2-(2,2-dibromoethenyl)-5-(4-methoxymethoxyphenyl)thiophene (8.8 g, 0.02 mole), prepared by the method of Example 6, ethanol (10 mL), and two drops of concentrated hydrochloric acid in tetrahydrofuran (50 mL) was stirred at room temperature for approximately 18 hours. Gaseous hydrogen chloride was bubbled into the mixture for several seconds, after which 10 mL of methanol was added. The resultant mixture was stirred at room temperature for two hours. This mixture was poured into an aqueous saturated ammonium chloride solution and extracted with diethyl ether. The ether extract was washed with an aqueous saturated ammonium chloride solution. The washed extract was dried over anhydrous magnesium sulfate and filtered. The filtrate was evaporated under reduced pressure, leaving a solid residue. This residue was dissolved in diethyl ether, and approximately 50 g of silica gel was added to the solution. The mixture was stirred briefly and filtered. The filtrate was evaporated under reduced pressure, yielding 7.8 g of 2-(2,2-dibromoethenyl)-5-(4-hydroxyphenyl)thiophene as a solid (mp 99°–101° C.).

Analysis: Calc'd for $C_{12}H_8Br_2OS$: C 40.03; H 2.24; Found: C 42.96; H 2.52.

EXAMPLE 34

2-(2,2-Dibromoethenyl)-5-(4-acetyloxyphenylene)thiophene

To a stirred mixture of 2-(2,2-dibromoethenyl)-5-(4-hydroxyphenyl)thiophene (1.0 g, 0.003 mole) and triethylamine (1.2 g, 0.08 mole) in tetrahydrofuran (20 mL) was added acetyl chloride (0.44 g, 0.0056 mole). The reaction mixture was stirred at room temperature for approximately 18 hours. The mixture was diluted with diethyl ether and washed in succession with an aqueous 5% sodium hydroxide solution, water, and an aqueous saturated sodium chloride solution. The washed mixture was dried over anhydrous magnesium sulfate and filtered. The filtrate was evaporated under reduced pressure, yielding 0.5 g of 2-(2,2-dibromoethenyl)-5-(4-acetyloxyphenyl)thiophene as a solid (mp 115°–115.5° C.).

Analysis: Calc'd for $C_{14}H_{10}Br_2O_2S$: C 41.82; H 2.51; Found: C 41.95; H 2.42.

EXAMPLE 41

2-(2,2-Dichloroethenyl)-5-(4-methylthiophenyl)thiophene

A solution of N,N-dimethylformamide (40 mL) and phosphorus oxychloride (8.8 mL) was stirred at 0° C. for ten minutes. A solution of 2-(4-methylthiophenyl)thiophene (1.5 g, 0.073 mole), prepared by the method of Example 6 from 2-bromothiophene and 4-methylthiophenyl magnesium bromide, dissolved in N,N-dimethylformamide (150 mL) was added. After complete addition, the mixture was stirred and heated on a steam bath for 4.5 hours. The reaction mixture was poured into a cold aqueous 15% sodium hydroxide solution. The resultant mixture was extracted, first with a 50:50 solution of diethyl ether and ethyl acetate, followed by ethyl acetate. The extracts were combined and dried over anhydrous magnesium sulfate. The dried extract was filtered, and the filtrate was evaporated under reduced pressure, leaving an oil which solidified upon standing. Purification of this solid by column chromatography on silica gel, eluting with n-hexane:ethyl acetate (80:20; 50:50), yielded 12.2 g of 5-(4-methylthiophenyl)thienyl-2-carboxaldehyde as a solid (mp 97°–98° C.)

In a manner similar to Example 10, the reaction of 5-(4-methylthiophenyl)thienyl-2-crboxaldehyde (3.0 g, 0.013 mole), hexamethylphosphorus triamide (33.4 g, 0.020 mole), and bromotrichloromethane (2.6 g, 0.013 mole) in methylene chloride (120 mL) produced 1.3 g of 2-(2,2-dichloroethenyl)-5-(4-methylthiophenyl)thiophene as a solid (mp 136°–139° C. )

Analysis: Calc'd for $C_{13}H_{10}Cl_2S_2$: C 51.83; H 3.35; Found: C 51.27; H 3.31.

EXAMPLE 42

2-(2,2-Dichloroethenyl)-5-(4-methylsulfonylphenyl)thiophene

To a stirred solution of 2-(2,2-dichloroethenyl)-5-(4-methylthiophenyl)thiophene (1.2 g, 0.0040 mole) in methanol (50 mL) was added a solution of potassium peroxymonosulfate (1.2 g, 0.0020 mole) in water (50 mL). After stirring for one hour at room temperature, an additional 0.3 g of potassium peroxymonosulfate was added, and a second addition of 0.3 g was made after an additional hour. After a total of about four hours of stirring at room temperature the mixture was extracted, first with diethyl ether, followed by methylene chloride. The extracts were combined and dried over anhydrous magnesium sulfate. The dried extract was filtered, and the filtrate was evaporated under reduced pressure leaving a solid residue. This residue was dissolved in isopropyl alcohol (15 mL), and a solution of potassium peroxymonosulfate (0.5 g) dissolved in about 5 mL of water was added. The resultant mixture was heated on a steam bath for approximately one hour. The mixture was diluted with 400 mL of water and cooled to 0° C. for one hour. A solid formed and was collected by filtration. The filter cake was dissolved in methylene chloride, and the solution was dried over anhydrous magnesium sulfate. The dried solution was filtered, and the filtrate was evaporated under reduced pressure, leaving a solid residue. This residue was purified by column chromatography on silica gel, eluting first with petroleum ether, followed by ethyl acetate, to yield 0.8 g of 2-(2,2-dichloroethenyl)-5-(4-methylsulfinylphenyl)thiophene as a solid (mp 124°–126° C.).

A mixture of 2-(2,2-dichloroethenyl)-5-(4-methylsulfinylphenyl)thiophene (0.8 g, 0.0025 mole) and m-chloroperbenzoic acid (2.0 g, 0.005 mole) in methylene chloride (50 mL) was stirred at room temperature for two days. The mixture was poured into a 0.5N aqueous sodium thiosulfate solution. The resultant mixture was extracted with diethyl ether. The extract was washed first with an aqueous 10% sodium hydroxide solution, followed by an aqueous 10% hydrochloric acid solution. The washed extract was dried over anhydrous magnesium sulfate and filtered. The filtrate was evaporated under reduced pressure, leaving a solid residue. This residue was purified by column chromatography on alumina, eluting with n-hexane:ethyl acetate (50:50), yielding 0.4 g of 2-(2,2-dichloroethenyl)-5-(4-methylsulfonylphenyl)thiophene as a solid (mp 143°–145° C.).

Analysis: Calc'd for $C_{13}H_{10}Cl_2O_2S_2$: C 46.85; H 3.02; Found: C 47.88; H 3.05.

EXAMPLE 47

2-(2,2-Dichloro-1-fluoroethenyl)-5-phenylthiophene

Under a dry nitrogen atmosphere, a stirred mixture of 2-phenylthiophene (1.0 g, 0.006 mole) and diethyl ether (0.6 mL) was cooled to 0° C. To this cold mixture was added n-butyllithium (3.0 mL of a 2.1M solution in hexanes). After complete addition, the mixture was allowed to warm to room temperature and was stirred for 45 minutes. This mixture was added to a cold (−30°C.), stirred solution of 1,1-dichloro-2,2-difluoroethene (1.2 g, 0.009 mole) in diethyl ether (0.6 mL), also under a dry nitrogen atmosphere. After complete addition, the reaction mixture was heated at reflux for four hours. The reaction mixture was allowed to cool to room temperature and was stirred for approximately 18 hours. The mixture was filtered, and the filtrate was evaporated under reduced pressure, leaving an only residue.

This residue was subjected to distillation under reduced pressure (80° C. at 0.1 mmHg), leaving a brown oil. This oil was dissolved in warm petroleum ether and, upon cooling, formed crystals. Collection of the crystals by filtration yielded 0.6 g of 2-(2,2-dichloro-1-fluoroethenyl)-5-phenylthiophene (mp 67°–68.5° C.).

Analysis: Calc'd for $C_{12}H_3Cl_2FS$: C 52.76; H 2.58; Found: C 52.69; H 2.60.

The following additional compounds were prepared by similar techniques, their identity being confirmed by elemental analysis and spectra.

| Example | Name | Melting Point (°C.) |
| --- | --- | --- |
| 1 | 2-(2,2-Dichloroethenyl)-5-phenylthiophene | 92–94 |
| 3 | 2-(2,2-Dibromoethenyl)-5-phenylthiophene | 105–106 |
| 4 | 2-(2,2-Dichloroethenyl)-4-methyl-5-phenylthiophene | |
| 5 | 2-(2,2-Dichloroethenyl)-4-methyl-5-(3-methylphenyl)thiophene | |
| 7 | 2-(2,2-Dibromoethenyl)-4-methyl-5-(3-methylphenyl)thiophene | |
| 8 | 2-(2,2-Dichloroethenyl)-4,5-diphenylthiophene | |
| 9 | 2-(2,2-Dibromoethenyl)-4,5-diphenylthiophene | |
| 11 | 2-(2,2-Dibromoethenyl)-3,5-diphenylthiophene | 125–130 |
| 12 | 2-(2,2-Dichloroethenyl)-3,4-dimethyl-5-thiophene | |
| 13 | 2-(2,2-Dibromoethenyl)-3,4-dimethyl-5-phenylthiophene | |
| 14 | 2-(2,2-Dichloroethenyl)-5-(2-methylphenyl)thiophene | 55–58 |
| 15 | 2-(2,2-Dibromoethenyl)-5-(2-methylphenyl)thiophene | 61–62 |
| 16 | 2-(2,2-Dibromoethenyl)-5-(2-methoxyphenyl)thiophene | 81–82 |
| 17 | 2-(2,2-Dichloroethenyl)-5-(3-methylphenyl)thiophene | 58–59 |
| 18 | 2-(2,2-Dibromoethenyl)-5-(3-methylphenyl)thiophene | |
| 19 | 2-(2,2-Dichloroethenyl)-5-[3-(1-methylethyl)phenyl]thiophene | |
| 20 | 2-(2,2-Dibromoethenyl)-5-[3-(1-methylethyl)phenyl]thiophene | |
| 21 | 2-(2,2-Dichloroethenyl)-5-(3-methoxyphenyl)thiophene | 62–64 |
| 22 | 2-(2,2-Dibromoethenyl)-5-(3-methoxyphenyl)thiophene | 63.5–65 |
| 23 | 2-(2,2-Dichloroethenyl)-5-(4-fluorophenyl)thiophene | 95–98 |
| 24 | 2-(2,2-Dichloroethenyl)-5-(4-methylphenyl)thiophene | |
| 25 | 2-(2,2-Dibromoethenyl)-5-(4-methylphenyl)thiophene | 115–116 |
| 26 | 2-(2,2-Dibromoethenyl)-5-[4-(1,1-dimethylethyl)phenyl]thiophene | |
| 28 | 2-(2,2-Dichloroethenyl)-5-(4-methoxyphenyl)thiophene | 115–117 |
| 29 | 2-(2,2-Dibromoethenyl)-5-(4-methoxyphenyl)thiophene | 126–127 |
| 30 | 2-(2,2-Dichloroethenyl)-5-(4-pentoxyphenyl)thiophene | 98–100 |
| 31 | 2-(2,2-Dibromoethenyl)-5-(4-pentoxyphenyl)thiophene | 94–95.5 |
| 32 | 2-(2,2-Dichloroethenyl)-5-(4-methoxymethoxyphenyl)thiophene | 79–80 |
| 33 | 2-(2,2-Dibromoethenyl)-5-(4-methoxymethoxyphenyl)thiophene | 72–75 |
| 35 | 2-(2,2-Dibromoethenyl)-5-(4-benzoyloxyphenyl)thiophene | 150–153 |
| 36 | 2-(2,2-Dibromoethyl)-5-(4-methoxycarbonyloxyphenyl)thiophene | 131–133 |

-continued

| Example | Name | Melting Point (°C.) |
|---------|------|---------------------|
| 37 | 2-(2,2-Dibromoethenyl)-5-(4-methyl-sulfonyloxyphenyl)thiophene | |
| 38 | 2-(2,2-Dibromoethenyl)-5-[4-(4-methyl-phenyl)sulfonyloxyphenyl)thiophene | |
| 39 | 4-[2-(2,2-Dibromoethenyl)-5-thienyl]-phenyl diethyl phosphate | |
| 40 | 2-(2,2-Dichloroethenyl)-5-(4-methyl-thiophenyl)thiophene | 116–118 |
| 43 | 2-(2,2-Dichloroethenyl)-5-(naphth-1-yl)thiophene | |
| 44 | 2-(2,2-Dibromoethenyl)-5-(naphth-1-yl)thiophene | |
| 45 | 2-(2,2-Dichloroethenyl)-5-(naphth-2-yl)thiophene | 115–118 |
| 46 | 2-(2,2-Dibromoethenyl)-5-(naphth-2-yl)thiophene | 107–109 |

In the normal use of the insecticidal and acaricidal thienyl compounds of the present invention, the thienyl compounds usually will not be employed free from admixture or dilution, but ordinarily will be used in a suitable formulated composition compatible with the method of application and comprising an acaricidally effective amount of thienyl compound. The thienyl compounds of this invention, like most pesticidal agents, may be blended with the agriculturally acceptable surface-active agents and carriers normally employed for facilitating the dispersion of active ingredients, recognizing the accepted fact that the formulation and mode of application of an acaricide may affect the activity of the material. The present thienyl compounds may be applied, for example, as sprays, dusts, or granules to the area where pest control is desired, the type of application varying of course with the pest and the environment. Thus, the thienyl compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the thienyl compounds. The granule particles are relatively large, a diameter of about 400–2500 microns typically. The particles are either impregnated with the thienyl compound from solution or coated with the thienyl compound, adhesive sometimes being employed. Granules generally contain 0.05–10%, preferably 0.5–5%, active ingredient as the acaricidally effective amount.

Dusts are admixtures of the thienyl compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the acaricide. These finely divided solids have an average particle size of less than about 500 microns. A typical dust formulation useful for controlling acarids contains 1 part of thienyl compound, such as 2-(2,2-dibromoethenyl)-4-methyl-5-phenylthiophene, and 99 parts of talc.

The thienyl compounds of the present invention may be made into liquid concentrates by dissolution or emulsification in suitable liquids and into solid concentrates by admixture with talc, clays, and other known solid carriers used in the pesticide art. The concentrates are compositions containing, as an acaricidally effective amount, about 5–50% thienyl compound and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

A typical 50% wettable powder formulation would consist of 50.0% (wt/wt) of 2-(2,2-dichloroethenyl)-3,5-diphenylthiophene, 22.0% attapulgite dilute, 22.0% kaolin diluent, and 6.0% sodium salts of sulfonated Kraft lignin emulsifier.

Typical carriers for solid concentrates (also called wettable powders) include fuller's earth, clays, silicas, and other highly absorbent, readily wetted inorganic diluents. A solid concentrate formulation useful for controlling acarids contains 1.5 parts each of sodium lignosulfonate and sodium lauryl-sulfate as wetting agents, 25 parts of 2-(2,2-dibromoethenyl)-4-methyl-5-phenylthiophene, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the thienyl compound with a liquid or solid emulsifying agent, or they may also contain a liquid carrier such as xylene, heavy aromatic naphthas, isophorone and other relatively nonvolatile organic solvents. For application, these concentrates are dispersed in water or ther liquid carriers and normally applied as sprays to areas to be treated.

A typical 50 gram per liter emulsifiable concentrate formulation would consist of 5.90% (wt/wt) of 2-(2,2-dibromoethenyl)-4-methyl-5-phenylthiophene; as emulsifiers; 1.80% of a blend of the calcium salt of dodecylbenzene sulfonate and a nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1.505 of a nonionic paste of polyalkylene glycol ether; and 88.10% refined xylene solvent.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyester alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the acaricidal composition.

Other useful formulations include simple solutions of the active ingredient in a solvent in which it is completely soluble at the desired concentration, such as acetone or other organic solvents.

An acaricidally effective amount of thienyl compound in an acaricidal composition diluted for application is normally in the range of about 0.001% to about 8% by weight. Many variations of spraying and dusting compositions known in the art may be used by substituting the thienyl compounds of this invention into compositions known or apparent in the art.

The acaricidal compositions of this invention may be formulated with other active ingredients, including other acaricides, nematicides, insecticides, fungicides, plant growth regulators, fertilizers, etc. In using the compositions to control acarids, it is only necessary that an acaricidally effective amount of thienyl compound be applied to the locus where control is desired. Such locus may, e.g., be the acarids themselves, plants upon which the acarids feed, or the acarid habitat. When the locus is soil, e.g., soil in which agricultural crops are or will be planted, the active compound may be applied to and optionally incorporated into the soil. For most applications, an acaricidally effective amount will be about 50 to 750 g per hectare, preferably 150 g to 500 g per hectare.

The acaricidal activity of the thienyl compounds whose preparation is described above was evaluated as follows:

The thienyl compounds were tested for acaricidal activity under normal ambient light as well as near ultraviolet light (wavelength (320–400 nanometer) at an intensity of 1600–2400 microwatts/cm² using test procedures adapted to the organisms in the test. Regardless of the organism, foliage of whole plants or foliage removed from whole plants was sprayed to runoff with a 105 acetone-0.25% octylphenoxypolyethoxyethanol-water solution containing up to 250 ppm of the test compound.

Leaves infested with adult twospotted spider mites (*Tetranychus urticae*) were removed from culture plants and cut into segments containing 50–75 female mites. Each segment was placed on the supper leaf surface of a whoe pinto bean (*Phaseolus vulgaris*) plant. After the mites had migrated to the under surfaces of the leaves, the leaf segments used to infest were removed and each plant sprayed with test chemical as described above. After the plants had dried, the entire plant and pot were placed in metal trays in a hood. A supply of water in the tray kept the plants turgid. Tests were conducted against both susceptible and phosphate resistant strains.

The test results were collected and recorded at the end of a 24 hour or 48 hour exposure period. The data obtained under ultraviolet irradiation appear in Table 1. In contrast to those data, in the absence of the ultraviolet light, and at a rate of 1000 rpm, the compounds gave zero kill in each case.

TABLE 1

| | | ACARICIDAL EFFICACY | | |
|---|---|---|---|---|
| Cmpd. of Ex. | Rate (ppm) | Exposure Time (Hr) | % Kill[1] | |
| | | | TSM-PR | TSM-R | TSM-S |
| 1 | 100 | 48 | | | 100 |
| 2 | 100 | 48 | | | 100 |
| 3 | 100 | 48 | 86 | 80 | 96 |
| 4 | 100 | 48 | | 18 | 100 |
| 5 | 50 | 24 | | | 57 |
| 6 | 100 | 48 | | 100 | 100 |
| 7 | 50 | 24 | | | 100 |
| 8 | 50 | 48 | | | 3 |
| 9 | 50 | 48 | | | 9 |
| 10 | 100 | 48 | | | 100 |
| | 32 | | | | 67 |
| 11 | 100 | 48 | | 100 | 100 |
| 12 | 100 | 48 | | | 100 |
| 13 | 100 | 48 | | 52 | 100 |
| 14 | 100 | 48 | | | 85 |

TABLE 1-continued

| | | ACARICIDAL EFFICACY | | |
|---|---|---|---|---|
| Cmpd. of Ex. | Rate (ppm) | Exposure Time (Hr) | % Kill[1] | |
| | | | TSM-PR | TSM-R | TSM-S |
| 15 | 100 | 48 | | | 13 |
| 16 | 250 | 48 | | | 100 |
| 17 | 100 | 48 | | 100 | 95 |
| 18 | 100 | 48 | | 100 | 100 |
| 19 | 50 | 24 | | | 41 |
| 20 | 50 | 24 | | | 7 |
| 21 | 100 | 48 | | | 97 |
| 22 | 100 | 48 | | | 100 |
| 23 | 100 | 48 | | 92 | |
| | 20 | 48 | | | 91 |
| 24 | 100 | 48 | | | 70 |
| 25 | 250 | 48 | | | 91 |
| 26 | 50 | 24 | | | 55 |
| 27 | 50 | 48 | | | 23 |
| 28 | 100 | 48 | | | 98 |
| 29 | 100 | 48 | | | 96 |
| 30 | 50 | 24 | | | 100 |
| 31 | 50 | 24 | | | 98 |
| 33 | 50 | 48 | | 55 | 60 |
| 34 | 50 | 48 | | | 74 |
| 35 | 50 | 48 | | | 11 |
| 36 | 50 | 24 | | | 4 |
| 37 | 50 | 48 | | | 80 |
| 38 | 50 | 48 | | | 76 |
| 39 | 100 | 24 | | 36 | |
| | 50 | 48 | | | 47 |
| 40 | 50 | 24 | | | 65 |
| 41 | 50 | 24 | | | 70 |
| 42 | 50 | 24 | | | 54 |
| 43 | 50 | 24 | | 100 | 100 |
| 44 | 50 | 24 | | | 97 |
| 45 | 50 | 24 | | 73 | 100 |
| 46 | 50 | 24 | | | 72 |
| 47 | 100 | 48 | | | 100 |

[1]Acarid species
TSM = twospotted spider mite (*Tetranychus urticae*)
-PR = Strain is resistant to tricyclohexyltin hydroxide
-R = Strain is resistant to phosphate insecticides
-S = Strain is not resistant to any types of insecticides

What is claimed is:

1. An acaricidal compound of the formula

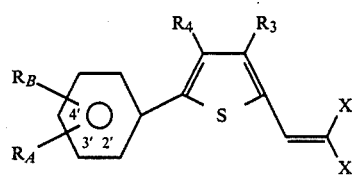

in which:
$R_A$ is hydrogen or a substituent at position 3' or 4' selected from lower alkoxy, fluoro, methoxymethoxy, 3'-methyl, 4'-methyl if X is bromo, methylcarbonyloxy, methylphenylsulfonyloxy, methylsulfonyloxy, methylsulfonyl, methylthio, or O,O-diethyl phosphonyloxy, $R_B$ is hydrogen or $R_A$ and $R_B$ together are —$C_4H_4$— bridging positions 2'-3+ or 3'-4';

$R_3$ is hydrogen, methyl, or phenyl;

$R_4$ is hydrogen or methyl; and

X is bromo or chloro.

2. An acaricidal compound of claim 1 in which:

(a) $R_A$ is hydrogen or a substituent at position 3' or 4' selected from lower alkoxy, methoxymethoxy, 3'-methyl, methylthio, or methylsulfonyl;

$R_B$ is hydrogen or $R_A$ and $R_B$ together are —$C_4H_4$— bridging positions 2'-3' or 3'-4';

$R_3$ is hydrogen, methyl, or phenyl;

$R_4$ is hydrogen or methyl; and
X is chloro; or (b) $R_A$ is hydrogen or a substituent at position 3' or 4' selected from lower alkoxy, fluoro, methoxymethoxy, methyl, methylcarbonyloxy, methylphenylsulfonyloxy, methylsulfonyloxy, methylthio, or O,O-diethyl phosphonyloxy;

$R_B$, $R_3$, and $R_4$ are as defined above; and
X is bromo.

3. 2-(2,2-Dibromoethenyl)-4-methyl-5-phenylthiophene, a compound of claim 1.

4. 2-(2,2-Dibromoethenyl)-3,4-dimethyl-5-phenylthiophene, a compound of claim 1.

5. 2-(2,2-Dichloroethenyl)-5-(naphth-1-yl)thiophene, a compound of claim 1.

6. 2-(2,2-Dibromoethenyl)-5-phenylthiophene, a compound of claim 1.

7. 2-(2,2-Dibromoethenyl)-5-(4-fluorophenyl)thiophene, a compound of claim 1.

8. 2-(2,2-Dibromoethenyl)-5-(4-acetyloxyphenyl)thiophene, a compound of claim 1.

9. 2-(2,2-Dibromoethenyl)-5-(4-methylsulfonyloxyphenyl)thiophene, a compound of claim 1.

10. 2-(2,2-Dichloroethenyl)-5-phenylthiophene, a compound of claim 1.

11. 2-(2,2-Dichloroethenyl)-4-methyl-5-phenylthiophene, a compound of claim 1.

12. 2-(2,2-Dibromoethenyl)-5-(3-methylphenyl)thiophene, a compound of claim 1.

13. An acaricidal composition comprising an acaricidally effective amount of at least one compound of claim 1 in admixture with an agriculturally acceptable carrier.

14. A method for controlling acarids which comprises applying to the locus where control is desired an acaricidally effective amount of at least one compound of claim 1.

* * * * *

UNITED STATES PATENT AND TRADEMARK OFFICE
CERTIFICATE OF CORRECTION

PATENT NO. : 4,782,079

DATED : November 1, 1988

INVENTOR(S) : Susan E. Burkart, Richard B. Phillips, David M. Roush

It is certified that error appears in the above-identified patent and that said Letters Patent is hereby corrected as shown below:

Column 3, line 12, "-20°C" should read -- -30°C--. Column 3, line 37, insert after "residue" -- to separate from the mixture. The liquid portion --. Column 4, line 40, "1.5g" should read -- 15.0g --. Column 8, line 44, "1.505" should read -- 1.50% --. Column 8, line 51, "polyester" should read -- polyether --. Column 9, line 30, "105" should read -- 10% --. Column 9, line 36, "supper" should read -- upper --. Column 10, line 58, "2'-3+" should read -- 2'3' --.

Signed and Sealed this

Twenty-fifth Day of December, 1990

Attest:

HARRY F. MANBECK, JR.

Attesting Officer  Commissioner of Patents and Trademarks